US00PP20802P2

(12) United States Plant Patent
Verschoor

(10) Patent No.: US PP20,802 P2
(45) Date of Patent: Mar. 2, 2010

(54) ***PHLOX* PLANT NAMED 'PINK LADY'**

(50) Latin Name: *Phlox paniculata*
Varietal Denomination: Pink Lady

(76) Inventor: Jan Verschoor, Mercelisvaartpad 17, Haarlem (NL) 2015 CS ( * ) Notice: Subject to any disclaimer, the term of this patent is extended or adjusted under 35 U.S.C. 154(b) by 0 days.

(21) Appl. No.: 12/316,161

(22) Filed: Dec. 10, 2008

(51) Int. Cl.
*A01H 5/00* (2006.01)

(52) U.S. Cl. ..... Plt./320

(58) Field of Classification Search ..... Plt./320
See application file for complete search history.

*Primary Examiner*—Annette H Para
(74) *Attorney, Agent, or Firm*—Audrey Charles

(57) ABSTRACT

A new and distinct cultivar of *Phlox* plant named 'Pink Lady', particularly distinguished by flowers colored a soft lilac pink with pure white centers, compact habit, healthy foliage, and good mildew resistance, is disclosed.

2 Drawing Sheets

Latin name of genus and species of plant claimed: *Phlox paniculata.*

Variety denomination: 'Pink Lady'.

BACKGROUND OF THE INVENTION

The present invention relates to a new and distinct cultivar of *Phlox* plant botanically known as *Phlox paniculata* and hereinafter referred to by the cultivar name 'Pink Lady'. The new cultivar originated from an open pollination in 2006 in a nursery location in Haarlem, The Netherlands between unknown male and female *Phlox paniculata* plants.

The new cultivar was selected from the results of the open pollination in 2007 in Haarlem, The Netherlands. Asexual reproduction of the new *Phlox* by vegetative cuttings in a controlled environment in Haarlem, The Netherlands since the summer of 2007, has shown that the unique features of the *Phlox* are stable and reproduced true to type in successive generations.

SUMMARY OF THE INVENTION

The following are the most outstanding and distinguishing characteristics of this new cultivar when grown under normal horticultural practices in Haarlem, The Netherlands:

1. Flowers colored a soft lilac pink with pure white centers;
2. Compact habit;
3. Healthy foliage; and
4. Good mildew resistance.

Of the many commercially available *Phlox* cultivars, the most similar in comparison to the new cultivar is 'Lavendelwolke', not patented. However, in side by side comparisons in Haarlem, The Netherlands, plants of the new cultivar 'Pink Lady' differ from plants of 'Lavendelwolke' by having healthier foliage, thicker stems, and a sturdier, more compact plant habit. Additionally, 'Pink Lady' flowers more evenly and earlier in the season with flowers that have a richer color than those of 'Lavendelwolke'.

In addition, plants of the new cultivar 'Pink Lady' are similar to 'Strawberry Daiquiri', U.S. Plant patent application No. 12/316,224. However, in side by side comparisons in Haarlem, The Netherlands, plants of the new cultivar 'Pink Lady' differ from plants of 'Strawberry Daiquiri' in flower color.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Pink Lady'. The plant was grown for approximately 1 year in a 1.5-liter container in Haarlem, The Netherlands in an outdoor nursery location.

The photograph on the first sheet is a side view of the overall growth and habit of 'Pink Lady'.

The photograph on the top of the second sheet is a close-up view of the inflorescence of 'Pink Lady'.

The photograph on the bottom of the second sheet is a close-up view of the foliage of 'Pink Lady'.

DETAILED BOTANICAL DESCRIPTION

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The data which define these characteristics were collected from asexual reproductions carried out in Haarlem, The Netherlands. The plant history was taken in September on 1-year-old plants in 1.5 liter containers which were planted and grown outdoors in daytime temperatures between 12° C. and 32° C. and nighttime temperatures between 4° C. and 16° C. No pinching, growth retardants or photoperiodic treatments were used. Observations were made when the plants were in natural daylight conditions.

Botanical classification: *Phlox paniculata* cultivar 'Pink Lady'.

Parentage:

*Female parent.*—Unknown *Phlox paniculata.*

*Male parent*—Unknown *Phlox paniculata.*

Propagation:

*Type cutting.*—Vegetative cutting.

*Time to produce a rooted cutting.*—Approximately 30 days with average soil temperature of 21° C.

*Root description.*—White, thin, fibrous, sparse.

*Rooting habit.*—Freely branching.

Plant description:

*Type.*—Herbaceous perennial. Overall shape: Narrow inverted triangle. High temperature tolerance: Tolerant to at least 35° C. Low temperature tolerance: Hardy to at least USDA Zone 4.

*Commercial crop time.*—Approximately 25 weeks from rooted cutting to finish in a 1.5 liter container.

*Growth habit and general appearance.*—Upright, low to moderately vigorous.

*Size.*—Height from soil level to top of plant plane: Approximately 33.1 cm. Width: Approximately 16.2 cm. Rate of growth: In spring, approximately 7 cm per month.

*Branching habit.*—Low to moderate basal branching; pinching will improve basal branching; flowering stems grow from base. Quantity of branches per plant: Approximately 2 flowering stems.

*Stem.*—Shape: Rounded. Strength: Strong. Aspect: Erect. Length to base of inflorescence: Approximately 16.2 cm. Diameter: Approximately 4.5 mm. Length of central internode: Approximately 2.6 cm. Texture: Glabrous, slightly glossy. Color of young and mature stems: 144A.

Foliage description:

*General description.*—Quantity of leaves per stem: Approximately 14. Form: Simple. Arrangement: Opposite. Durability to stress: High.

*Leaves.*—Shape: Oblanceolate, slightly carinate. Margin: Slightly revolute, very short and finely serrate with approximately 30 teeth per cm. Apex: Acute. Base: Attenuate. Venation pattern: Pinnate. Length of mature leaf: Approximately 9.5 cm. Width of mature leaf: Approximately 3.2 cm. Texture of upper and lower surfaces: Smooth, glabrous. Color of upper surface of young foliage: 147A with venation of 144C to 144D. Color of lower surface of young foliage: 147B with venation of 144C to 144D. Color of upper surface of mature foliage: Between 137B and 146A with venation of 144C to 144D. Color of lower surface of mature foliage: 146B with venation of 144C to 144D.

*Petiole.*—Shape: V-shaped. Length: Approximately 2.0 mm. Width: Approximately 3.0 mm. Height: Approximately 2.5 mm. Color: 144C to 144D.

Flowering description:

*Flowering habit.*—Freely flowering under outdoor growing conditions with substantially continuous blooming from summer through late summer.

*Lastingness of flower on the plant.*—Approximately 10 days.

*Flowering response time.*—Approximately 60 days.

Inflorescence description:

*General description.*—Type: Compound terminal panicle, self-cleaning. Fragrance: Moderately, sweet and pleasant; typical *Phlox paniculata* scent. Height: Approximately 17.9 cm. Width: Approximately 15.3 cm. Quantity of opened flowers per inflorescence: Approximately 50. Rate of flower opening: Approximately 20% of the flowers at any stage.

*Peduncle.*—Strength: Strong. Aspect: Erect primary peduncles with secondary peduncles at approximately a 45° angle. Length of primary: Approximately 15.1 cm. Diameter of primary: Approximately 3.0 mm. Length of secondary: Approximately 3.6 cm. Diameter of secondary: Approximately 1.5 mm. Texture: Smooth, glabrous. Color: Primary peduncles 144A with darker secondary peduncles of 146B to 146C.

Flower description:

*General description.*—Type: Single. Shape: Salverform. Aspect: Upright to outward.

*Bud just before opening.*—Quantity per inflorescence: Approximately 50. Shape: Oblanceolate. Length: Approximately 1.7 cm. Diameter: Approximately 6.0 mm. Color: Petals of 76B to 76C; calyx base of 145B to 145C transitioning to 187A toward apex. Rate of opening: Approximately 4 days.

*Corolla.*—Depth: Approximately 2.8 cm. Diameter: Approximately 3.3 cm.

*Petals.*—Quantity: 5, lower 55% of each petal fused into a narrow tube. Arrangement: Rotate. Appearance: Dull. Shape, lobe: Spathulate. Margin: Entire. Apex: Broadly rounded. Length: Approximately 3.2 cm. Length of free portion: Approximately 1.5 cm. Width: Approximately 1.9 cm. Texture of upper and lower surfaces: Smooth. Color of upper surface when first open: Upper half of free part of each petal N82C with the lower half closest to but whiter than 155C, tube of N77D. Color of lower surface when first open: 85C with the tube of N77D. Color of upper surface when fully open: Upper half of free part of each petal N80D to slightly lighter with the lower half closest to but whiter than 155C, tube of N77D. Color of lower surface when fully open: 85C with the tube of N77D.

*Calyx.*—Shape: Campanulate. Length: Approximately 1.0 cm. Diameter: Approximately 4.0 mm.

*Sepals.*—Quantity: 5, lower third fused into a narrow tube. Arrangement: In a single whorl. Appearance: Moderately glossy. Shape: Linear. Margin: Entire. Apex: Narrow apiculate. Length: Approximately 9.0 mm. Width: Approximately 1.2 mm. Texture of upper and lower surfaces: Smooth. Color of upper and lower surfaces of immature sepals: 187A with 146C at base. Color of upper and lower surfaces of mature sepals: 187A with 146C at base.

*Pedicel.*—Strength: Strong. Aspect: Erect when directly adjoining peduncle, others at an approximately 60° angle. Length: Approximately 3.0 mm. Diameter: Approximately 1.0 mm. Texture: Smooth, glabrous. Color: 146B to 146C.

*Reproductive organs.*—Androecium: Stamen quantity: 5 per flower, basifixed. Anther shape: Oblong. Anther length: Approximately 2.0 mm. Filament length: Approximately 1.0 mm. Anther color: 8C to 8D. Pollen amount: Moderate. Pollen color: 11 C to 11D. Gynoecium: Pistil quantity: 1 per flower. Pistil length: Approximately 1.2 cm. Stigma shape: Cleft (3-parted). Stigma color: 150D. Style length: Approximately 1.1 cm. Style color: 182D. Ovary color: 143A.

Seed and fruit production: Neither seed nor fruit production has been observed.

Disease and pest resistance: Good mildew resistance. No particular resistance or susceptibility to other diseases or insects noted to date.

What is claimed is:

1. A new and distinct cultivar of *Phlox* plant named 'Pink Lady', substantially as herein shown and described.

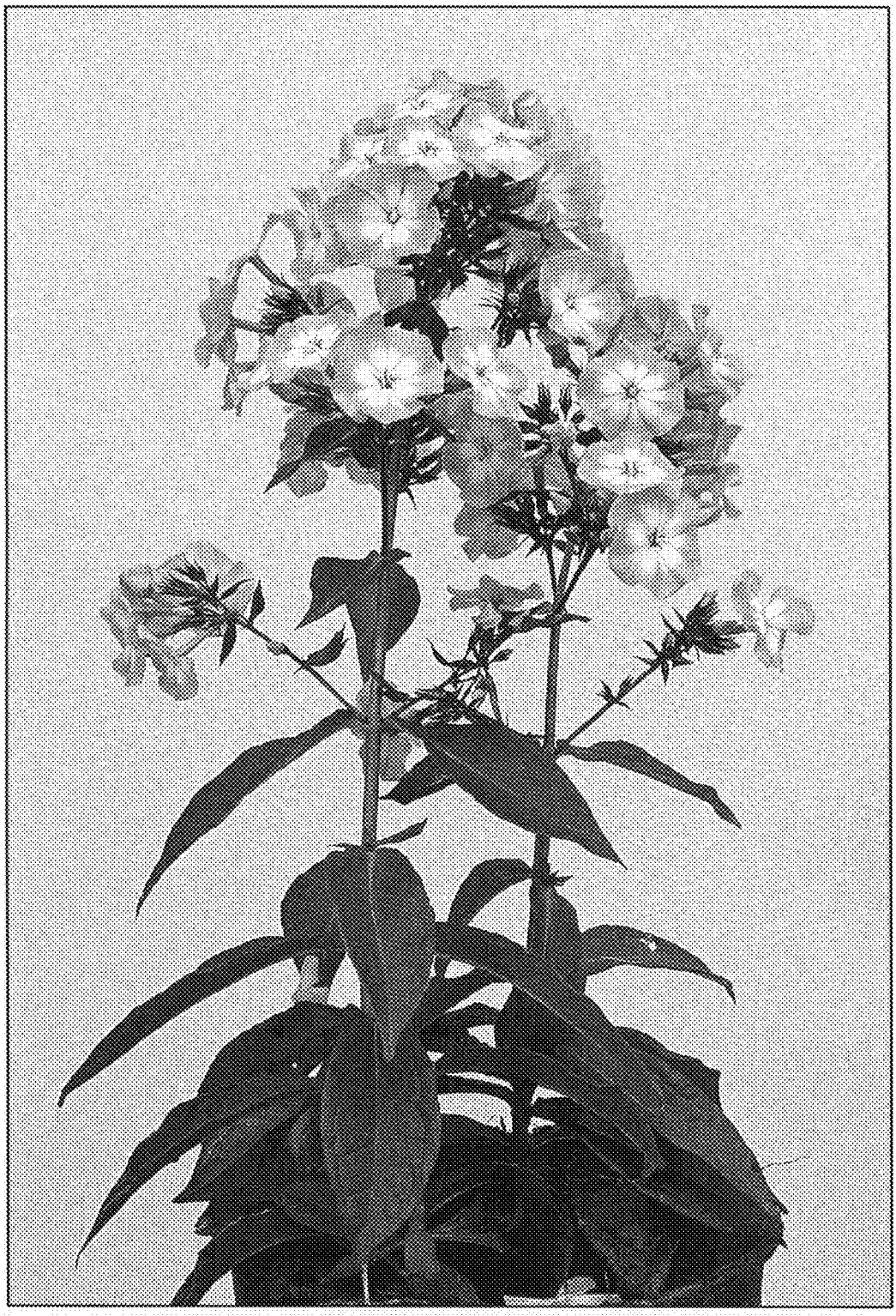

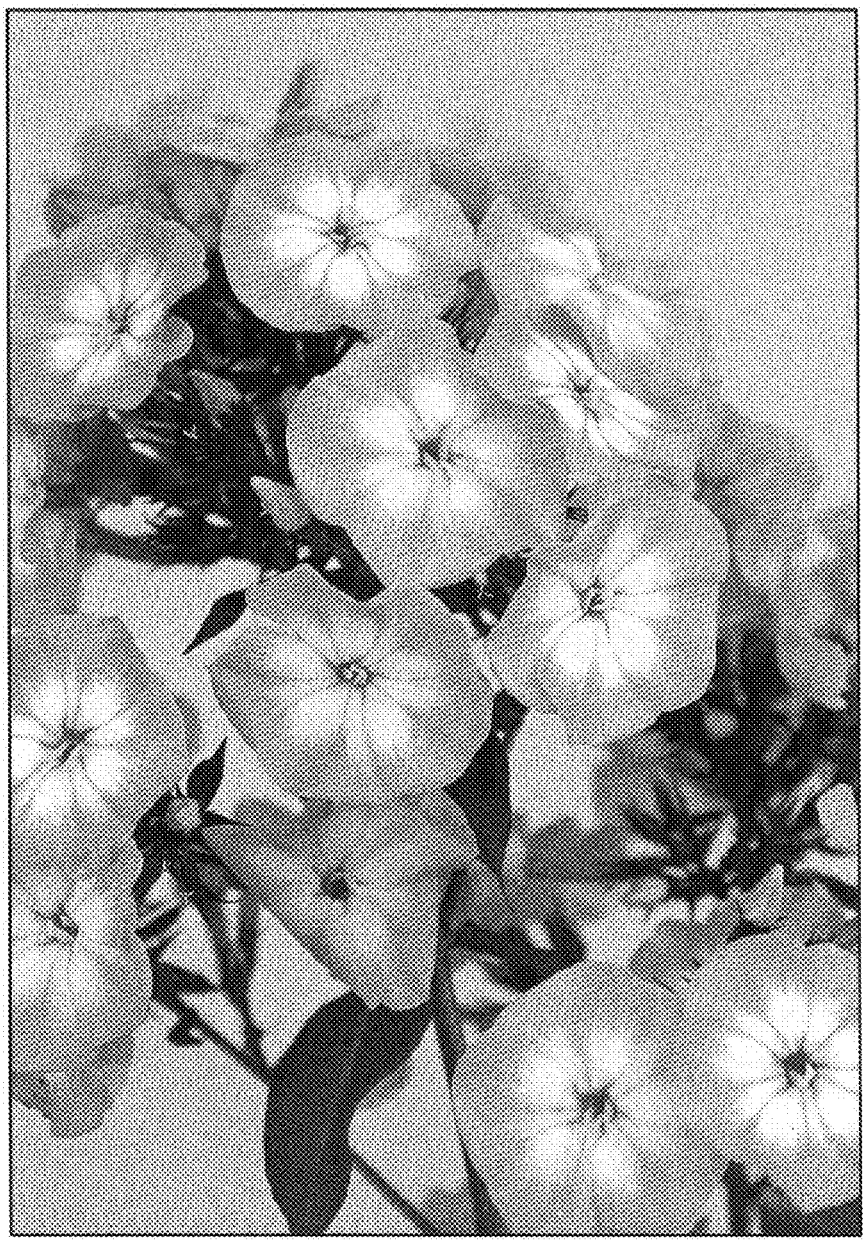
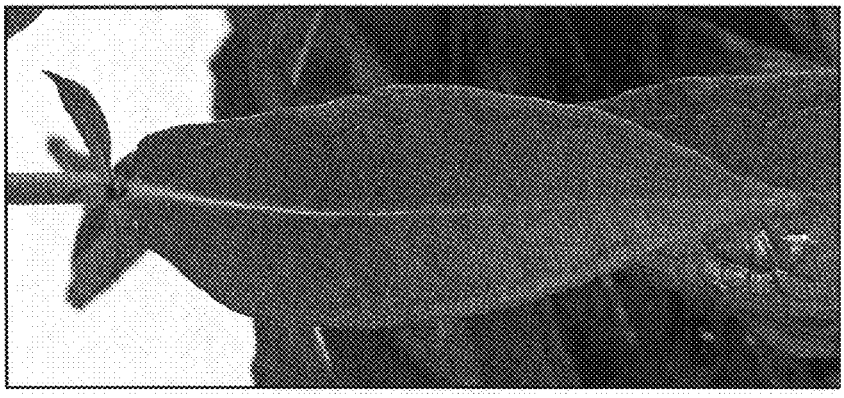

* * * * *